(12) United States Patent
Chang et al.

(10) Patent No.: US 7,508,523 B2
(45) Date of Patent: Mar. 24, 2009

(54) INTERFEROMETRIC SYSTEM FOR COMPLEX IMAGE EXTRACTION

(75) Inventors: Shoude Chang, Ottawa (CA); Costel P. Flueraru, Ottawa (CA); Sherif S. Sherif, Gloucester (CA)

(73) Assignee: National Research Council of Canada, Ottawa, Ontario (CA)

( * ) Notice: Subject to any disclaimer, the term of this patent is extended or adjusted under 35 U.S.C. 154(b) by 60 days.

(21) Appl. No.: 11/779,962

(22) Filed: Jul. 19, 2007

(65) Prior Publication Data

US 2008/0198367 A1 Aug. 21, 2008

Related U.S. Application Data

(60) Provisional application No. 60/832,612, filed on Jul. 24, 2006.

(51) Int. Cl.
 *G01B 9/02* (2006.01)
(52) U.S. Cl. ...................................... 356/479
(58) Field of Classification Search ................... 356/479
 See application file for complete search history.

(56) References Cited

U.S. PATENT DOCUMENTS

| | | | |
|---|---|---|---|
| 6,404,535 B1 * | 6/2002 | Leight | 359/326 |
| 6,657,727 B1 | 12/2003 | Izatt et al. | |
| 7,019,838 B2 | 3/2006 | Izatt et al. | |
| 2008/0137094 A1 * | 6/2008 | Teramura et al. | 356/489 |
| 2008/0140328 A1 * | 6/2008 | Kuroiwa | 702/66 |

OTHER PUBLICATIONS

"Oxygen Saturation—Dependent Absorption and Scattering of Blood", Faber et al, Phys. Rev. Ltrs, V. 93, No. 2, Jul. 9, 2004.

* cited by examiner

*Primary Examiner*—Tarifur Chowdhury
*Assistant Examiner*—Jonathan D Cook
(74) *Attorney, Agent, or Firm*—Teitelbaum & MacLean; Neil Teitelbaum; Doug MacLean (57) ABSTRACT

The invention provides an interferometric system and method for quadrature detection of optical characteristics of a sample. The system includes a Mach-Zehnder interferometer providing a variable optical delay between light collected from the sample and reference light. The Mach-Zehnder interferometer has an output M×N coupler with N≧3 output ports. Two differential detectors, each having two input ports coupled to a different two of the N output ports of the M×N coupler, produce first and second electrical signals having an interferometric phase shift. A processor is provided for computing real and imaginary parts of a complex refractive index of the sample from the first and second electrical signals by using complex deconvolution.

18 Claims, 6 Drawing Sheets

INTERFEROMETRIC SYSTEM FOR COMPLEX IMAGE EXTRACTION

CROSS-REFERENCE TO RELATED APPLICATIONS

The present invention claims priority from U.S. Provisional Patent Application No. 60/832,612 filed Jul. 24, 2006, entitled "Apparatus and method for complex image extraction and restoration with application in optical coherence tomography (OCT) and optical low coherence reflectometry (OLCR)", which is incorporated herein by reference.

TECHNICAL FIELD

The present invention relates to optical interferometric systems, and in particular to an interferometric system and method for simultaneously obtaining absorptive and refractive properties of a sample with a high signal to noise ratio.

BACKGROUND OF THE INVENTION

Optical Coherence Tomography (OCT) and Optical Low Coherence Reflectometry (OLCR) are interferometry-based techniques that have been successfully used in non-invasive and non-destructive analysis and imaging of structures in turbid media, especially in biological tissues. OLCR is a one-dimensional optical ranging technique where the amplitude and longitudinal delay of broadband light scattered from a sample is resolved using a low-coherence interferometer. OCT constructs a two-dimensional transverse image of the sample from a series of one-dimensional scans; it is a non-invasive, non-destructive and non-contact imaging method that typically uses a low coherence interferometer to extract depth-resolved sample information, and a scanning system to build a 2D image. Recently, Fourier-domain OCT techniques such as swept-source OCT (SS-OCT) that utilizes a narrow-line swept-wavelength laser source have also been disclosed. Both OCT and OLCR techniques allow the localization of reflecting sites within a transparent or semi-transparent sample with a micrometer spatial resolution.

In both of these interferometric techniques, broadband or swept-frequency light traveling a reference path is mixed on the surface of a single or multiple detectors with light returning from or traversing a sample. With a broad-band light source, a variable delay line in the reference arm is used to select a small range of depth, conventionally referred to as the "coherence gate", within the sample wherefrom the reflected or scattered signal results in interferometric fringes that can be detected and processed. The position of the coherence gate is defined and controlled by matching the optical path in two interferometer arms using the variable delay line.

Particular OCT implementations may take the form of a time-domain OCT or frequency domain OCT. Time-domain OCT is based on heterodyne interferometry, wherein light from the sample is combined with frequency shifted reference light, with the frequency shift resulting either from passing through an optical modulator located in the reference arm, or from the Doppler effect when the reference light is reflected from a moving reference mirror. Mixing of the sample and reference light in a square-law detector results in an electrical signal having DC and AC frequency components. The AC frequency component, which is caused by the interference of the sample light with the time-delayed reference light, is processed to extract sample information.

In the Fourier domain OCT the reference mirror position is fixed during the measurement, and the OCT setup is based on homodyne interferometry. The complete interferometric signal consists of DC components arising from non-mixing light from each of the arms, and interferometric components arising from mixed light.

Figure 1:
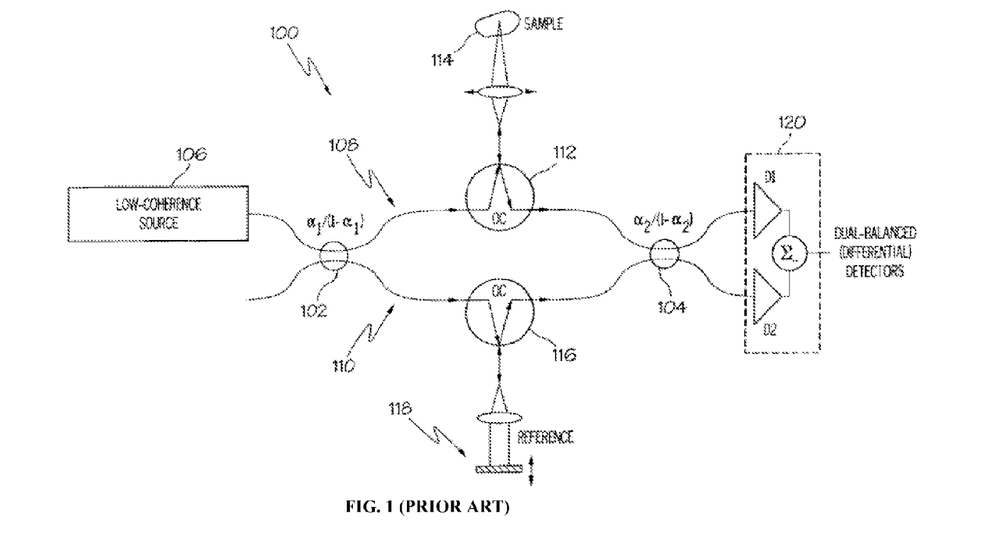
FIG. 1 is a diagram of a prior-art OCT system using balanced detection.

The central part in both homodyne and heterodyne OCT systems is an interferometer, typically of a Michelson or a Mach-Zehnder type, illuminated for example by a low coherence light source. FIG. 1 illustrates a prior-art Mach-Zehnder-based OCT system 100 that is disclosed in U.S. Pat. No. 6,657,727 issued to Izatt et al, which is incorporated herein by reference; this interferometer can be implemented using inexpensive semiconductor light sources, e.g. wide-band LEDs, commercially available detectors, and flexible single-mode optical fibers suitable for remote imaging through minimally invasive diagnostic instruments.

In the OCT system 100, a Mach-Zehnder interferometer formed using two 2×2 couplers 102 and 104 is illuminated by a broadband light source 106; a sample 114 under examination is placed in a sample arm 108. A reference arm 110 includes a reflective delay line formed using a movable mirror 118, which is inserted into the reference arm 110 through a circulator 116. The sample arm 108 includes another circulator 112 which serves to illuminate the sample 114 with light coupled into the sample arm 108 by the coupler 102, and to direct light reflected from the sample 114 into the output coupler 104, wherein it is combined with light from the reference arm 110 and passed via its two output ports onto a balanced receiver 120, which includes two photo detectors D1 and D2 with differentially connected outputs. Due to the limited coherence length of the source, typically 10-15 microns, light transmitted through the reference arm 110 and light backscattered by internal sample reflections interferes constructively or destructively only when the interferometer arm optical path lengths are matched to within the source coherence length. Scanning the reference arm 110 length through a position corresponding to the depth of a reflecting site within the sample generates a localized interference pattern, which is recorded as a localized modulation of the detector current as a function of the reference arm position. The balanced receiver 120 current generated by a sample containing multiple reflecting sites distributed along its depth, such as biological tissue, contains the sum of multiple, overlapping copies of this interference pattern. A map of tissue reflectivity versus depth, which is conventionally referred to as an A-Scan, is obtained by scanning the reference mirror 118 at constant velocity, while recording the envelope of the detector current, e.g. by demodulating the detector current at the resulting Doppler frequency. Cross-sectional images of the sample backscatter, typically referred to as "B-Scans", may be acquired by obtaining sequential A-scans while scanning the probe beam across the tissue surface using a lateral scanning optic device. The resulting two-dimensional datasets are plotted as gray-scale or false-color images.

When the optical path difference for light raveling in the reference and sample arms of a low-coherence interferometer is zero, the OCT receiver 120 generates a signal which has an interferometric component $I_{s\ max}$. As the optical path difference increases far beyond the coherence length of the used source, the receiver generates a noise signal which is conventionally characterized by the standard deviation $\sigma_i$ of the receiver photocurrent. The signal to noise ratio (SNR) $I_{s\ max}^2/\sigma_i^2$ is an important characteristic of an OCT interferometer, which defines the image contrast for the sample.

To obtain a high-contrast image from a turbid medium, such as a biological sample, an imaging system should have a high SNR. A significant advantage of using a low-coherence interferometer, such as the interferometer 100, for signal detection is that the mixing of the reference light with the light scattered from the sample at the square-low detector provides a dramatic increase in the signal to noise ratio (SNR) and the dynamic range, as compared to direct detection of the scattered light. Indeed, since the interferometric component of the detector current is proportional to the product of the electric field amplitudes returning from each arm, the detected envelope signal is proportional to the square root of the sample reflectivity; as the result, very small reflections in the sample on the order of $10^{-11}$ of the incident power can be detected in A-scans recorded in a fraction of a second.

The Mach-Zehnder based interferometric system 100 shown in FIG. 1 provides additional SNR gain by optimizing the power splitting ratio $\alpha_1$ of the optical coupler 102, and by using a balanced differential receiver 120 instead of a single photo detector. As described in U.S. Pat. No. 6,657,72, the dual-balanced detection has two advantages: first, the light intensity incident on detectors D1 and D2 as a function of reference arm delay is 180° out of phase due to a known property of a 2×2 coupler, so that the envelope of difference signal between the two detector currents is equal to twice the amplitude of the AC component of the photocurrent of each detector; and, secondly, any excess noise originated from the low-coherence source 106 will be common to both detectors and therefore will be eliminated by the difference operation.

The interferometric component of the receiver 120 signal depends sinusoidaly on the optical path length difference between the arms of the interferometer, and also on any additional phase delay between the reference and sample arm fields. When this phase term is zero, the interferometric signal varies as a cosine of the optical path length difference between the arms, and when the phase term is 90 degrees, the interferometric signal varies as a sine of the path length difference. The zero and 90 degree phase delayed versions of the interferometric signal are commonly referred to as the real and imaginary components, or zero and 90 degree quadrature components, of a complex interferometric signal I.

A limitation of the interferometric system 100, as well as many other prior-art interferometric systems used in Fourier domain OCT imaging, is that it provides only one of two quadrature components of the interferometric signal resulting from the mixing the sample and reference light, or, equivalently, only a real part of a complex interferometric signal, so that information carried by the imaginary part of the signal is lost. One drawback resulting from this limitation of conventional single-channel OCT systems is the appearance of the co-called complex conjugate artifact, due to which positive and negative distances in an OCT scan are not resolved, so that only half of the potentially available imaging depth can be realized.

Another drawback of the prior-art single-channel OCT systems is that the detected interferometric signal typically depends on both the refractive and absorptive properties of the imaged sample, and it becomes difficult to separate them and obtain refractive and absorptive properties of the imaged sample individually. Prior-art attempts at such separation have been based on so-called Kramers-Kronig (KK) relations, which connect frequency dependencies of real and imaginary parts of a complex refractive index in one integral relationship. This, however, requires first acquiring, for example, the absorption coefficient of a sample in a wide spectral range, before the refraction coefficient of the sample at a given frequency can be computed. This approach has considerable drawbacks, since it requires expensive widely-tunable sources of light for performing OCT measurements over a wide wavelength range, for example from 200 nm to 1000 nm, with a relatively small frequency step, and the results of KK-computations are very sensitive to the accuracy of the initial absorption spectra measurements. An example of such approach is disclosed, for example, in an article entitled "Oxygen Saturation-Dependent Absorption and Scattering of Blood", by Dirk J. Faber et al, published in Phys. Rev. Letters, V. 93, No 2, 9 Jul. 2004.

Figure 2:
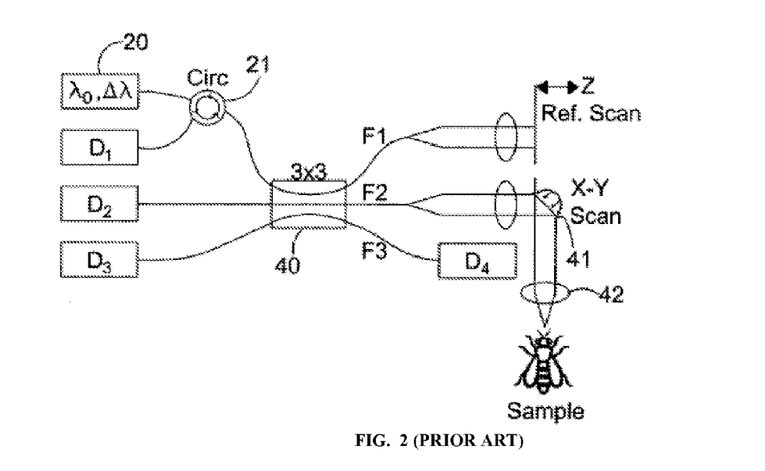
FIG. 2 is a diagram of a prior-art OCT system using a 3×3 coupler to provide quadrature signals.

U.S. Pat. No. 7,019,838 to Izatt et al, which is incorporated herein by reference, discloses an OCT system that is enhanced for simultaneous acquisition of both quadrature components of the complex interferometric signal; the system, which is shown in FIG. 2 corresponding to FIG. 9 of the '838 patent, is based on a 3×3 optical coupler 40 used as a beamsplitter in a Michelson interferometer configuration, and uses specific optical properties of optical couplers having more than 2 optical ports. In particular, light entering a 3×3 optical coupler via two of its input ports will exit the coupler with a phase shift of 120°, or 2π/3, between light intensity outputs from any two of the three ports, provided that the coupler evenly splits the light between the output ports. In the shown configuration, the broadband light from the source 20 is coupled into one input port of the coupler 40 via a circulator 21. The coupler 40 splits the light along fibers F1 and F2 which respectively lead to the reference and sample arms. The reference arm terminates with a reflector providing a variable optical delay; the sample shown as a fly serves as the reflection source of the other arm. Light beams reflected from the reference and sample arms are re-combined in coupler 40. Two portions of this re-combined light are then detected by detectors D2 and D3, and a third portion of this light is input into coupler 2, where it is detected by detector D1. Each channel of the interferometer, i.e. each of the detectors D1-D3, measures an output signal with a phase shift of 120° relative to the other two output channels. Using the output signals of any two channels, the real and imaginary components of the complex ac interferometric signal can be obtained.

One drawback of the OCT system shown in FIG. 2 is that it lacks balanced detectors that enable to eliminate common mode noise in system 100 shown in FIG. 1, and the description in '838 patent does not provide any clear way how the differential detection can be realized in the system described therein. Another drawback of this system is that it is based on a Michelson configuration with a single coupler 40 functioning both as a beam splitter and a beam combiner, which does not allow the same flexibility as a Mach-Zehnder configuration in optimizing optical power splitting between the reference and sample arms. In a further disadvantage, about one third of the optical power of the source 20, which is directed along fiber F3, does not contribute in the interferometric signal. Also, the '838 patent does not provide a way to obtain refractive and absorptive properties of the sample using the disclosed system.

An object of the present invention is to provide an interferometric system that employs differential detection to obtain both quadrature components of a complex interferometric signal with enhanced SNR.

Another object of the present invention is to provide an interferometric system and method to generate refraction and absorption properties of a sample simultaneously by utilizing both quadrature components of a complex interferometric signal that is obtained using differential detection.

SUMMARY OF THE INVENTION

In accordance with the invention, a system is provided for detecting optical characteristics of a sample, comprising an interferometer for mixing light collected from the sample with reference light for interfering therewith, the interferometer comprising:

a first optical coupler having two input ports connected for receiving reference light and light collected from the sample, and at least three output ports;

a first differential detector having two input optical ports coupled to a first two of the at least three output ports of the optical coupler for providing a first electrical signal having a first interferometric component; and, a second differential detector having two input optical ports coupled to a second two of the at least three output ports of the optical coupler for providing a second electrical signal having a second interferometric component;

wherein the first optical coupler is such that the first and second interferometric components have a relative phase shift there between that is not an integer multiple of $\pi$, so as to provide information separately characterizing real and imaginary components of a complex interferometric signal related to the sample.

The interferometer is of a Mach-Zehnder type, and includes a first beam splitter having two output ports coupled to the two input ports of the first optical coupler using two connecting arms, and an input port, one of the connecting arms including a time delay means for providing a variable optical time delay to light propagating in said connecting arm.

In accordance with one embodiment of this invention, one of the connecting arms comprises a sample illuminating means for illuminating the sample and for directing the light collected from the sample to one of the input ports of the first optical coupler.

In accordance with another embodiment, a sample illuminating means for illuminating the sample is positioned optically before the first beam splitter and is for directing light reflected from the sample to the input port of the first beam splitter via an optical circulator; it includes a partially transmissive reference reflector for illuminating the sample there through and for providing the reference light to the input port of the first beamsplitter vie the optical circulator, said reference reflector forming a Fizeau interferometer with the sample.

Another aspect of the present invention provides a method for simultaneously obtaining refractive and absorptive properties of a sample, the method comprising the steps of: a) illuminating the sample with a portion of broadband light and collecting light from the sample; b) providing light collected from the sample to an input port of an M×N optical coupler having M input ports and N output ports, while simultaneously providing a reference portion of the broad band light into another input port of the M×N optical coupler, wherein $N \geq 3$ and $M \geq 2$; c) coupling light from a first two of the N output ports of the M×N coupler into a first differential detector to obtain a first electrical signal; d) coupling light from a second two of the N output ports of the M×N coupler into a second differential detector to obtain a second electrical signal; e) generating real and imaginary parts of a complex interferometric signal from the first and second differential signals; f) performing complex deconvolution of the complex interferometric signal and a coherence function of the broadband light to obtain depth-resolved complex scattering function of the sample; and, g) computing real and imaginary parts of a complex refractive index of the sample from the real and imaginary parts of the depth-resolved complex scattering function of the sample.

Another aspect of the present invention provides an interferometric system for detecting optical characteristics of a sample, comprising: a Mach-Zehnder interferometer for providing a variable optical delay between light collected from the sample and reference light, the Mach-Zehnder interferometer comprising an output M×N coupler for mixing the light collected from the sample with the reference light for interfering therewith, the M×N coupler having $N \geq 3$ output ports; and, first and second differential detectors, each having two input ports coupled to a different two of the N output ports of the M×N coupler, for producing first and second electrical signals having an interferometric phase shift there between, wherein said interferometric phase shift is not equal to an integer multiple of $\pi$ radians. A processor is provided for computing real and imaginary parts of the complex refractive index of the sample from the first and second electrical signals using complex deconvolution.

BRIEF DESCRIPTION OF THE DRAWINGS

The invention will be described in greater detail with reference to the accompanying drawings which represent preferred embodiments thereof, in which like elements are labeled using like reference numerals, and wherein.

DETAILED DESCRIPTION

The present invention is a novel interferometric system and method for OCT and OCDR which employ differential balanced detection for simultaneous acquisition of quadrature components of a complex interferometer signal, and for obtaining there from optical characteristics of a sample such as absorption and refraction parameters.

Exemplary embodiments of the interferometric system of the present invention are shown in FIGS. 3, 4, 8 and 10 and are hereafter described.

Figure 3:
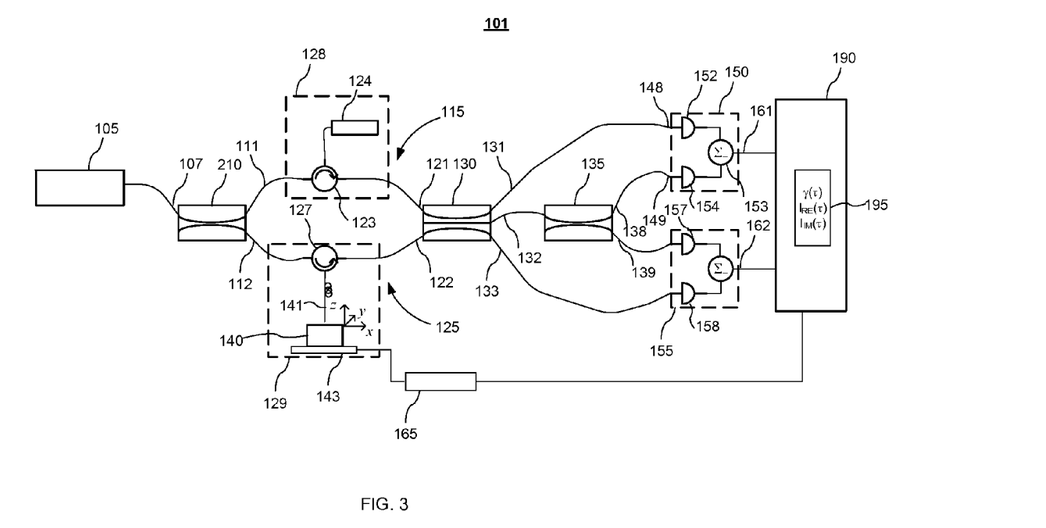
FIG. 3 is a diagram of a first embodiment of the interferometric system of the present invention utilizing a 3×3 coupler followed by a single 2×2 coupler.

With reference to FIG. 3, in a first embodiment of the invention an interferometric system 101 includes a Mach-Zehnder interferometer formed by a beamsplitter 210, hereinafter also referred to as the first beamsplitter, and a multiport coupler 130, hereinafter also referred to as the first coupler. The beamsplitter 210 has an input port 107 and two output ports 111 and 112, which are coupled to respective input ports 121 and 122 of the first coupler 130 by two connecting arms 115 and 125. In the shown example the beam splitter 210 is embodied as a 2×2 waveguide, for example fiber-optic, directional coupler having one of the input ports unused and will also be referred to hereinafter as the 2×2 coupler 210; alternatively the beam splitter 210 can be embodied using bulk optics or any other suitable optical power splitting device known in the art. One of the connecting arms of the Mach-Zehnder interferometer, i.e. the first arm 115 includes adjustable time delay means 120 formed in this embodiment by a circulator 123 and a variable reflective optical delay line 124, for example as shown in FIG. 1; the arm 115 will also be referred to herein as the reference arm 115. As one skilled in the art will appreciate, alternative designs of the adjustable time delay means are also possible and can be used herein, for example those operating in transmission rather than reflection, thereby eliminating the need for the circulator 123. The reference arm 115 may also include an optical attenuator for adjusting the optical power in the reference arm to a desired value.

The second arm 125, which also be referred to herein as the sample arm 125, includes sample illuminating means for illuminating a sample 140 which is to be investigated, and for directing light collected from the sample along the sample arm 125 into the second input port 122 of the coupler 130. In the shown embodiment, the sample illuminating means are formed by a circulator 127 and a section of a single-mode optical fiber 141, which may have a lensed end for focusing light onto a desired location on or within the sample 140 for locally illuminating thereof and for collecting scattered light as known in the art. In other embodiments, the sample illuminating means can include other focusing or collimating optical elements such as bulk of fiber-optic lenses, and may be arranged so as to collect light transmitted through the sample 140, in which case the circulator 127 can be eliminated.

An advantage of the Mach-Zehnder configuration, as compared to a Michelson interferometer configuration, is that the power splitting ratio of the 2×2 coupler 210 can be optimized so as to direct most of the light onto the sample 140; this can be especially important for biological samples which typically reflect only a very small portion of light back into the fiber end 141, so that an overall transmission coefficient $T_S$ of the sample arm 125 is small. By way of example, the splitting ratio of the 2×2 coupler 210 is selected to be 90:10, with about 90 percent of light exiting the coupler 210 being directed along the sample arm 125 towards the sample 140.

The reference light from the reference arm 115 and the sample light from the sample arm 125 is re-combined in the first coupler 130 with a relative time delay τ there between that is set and can be scanned by the variable time delay 124 inserted into the reference arm 115 via the circulator 123.

Contrary to the prior art Mach-Zehnder based OCT interferometers such as the one shown in FIG. 1, in the present invention the coupler 130 at the output of the Mach-Zehnder interferometer is not a conventional 2×2 coupler, but a multiport M×N coupler, where the number of output ports N is at least 3 or more, while the number M of the input port is at least two. One type of an M×N coupler with M<N is an N×N directional coupler wherein only M of the N input ports are used. Such couplers are known in the art, for example fusedfiber couplers wherein 3 or more optical fibers are fused together over a selected length so as to effect evanescent field coupling there between; relevant properties of these couplers are described in further detail, for example, in the U.S. Pat. No. 7,019,838 which is incorporated herein by reference. Such couplers can be characterized by coupling coefficients $α_{i,j}$ describing which fraction of radiation received into i-the input port exits the coupler via a j-the output port. For example, a 2×2 coupler may have a 50/50 splitting ratio where $α_{i,1}=α_{i,2}=½$, i=1, 2, and a 3×3 coupler may have a 33/33/33 splitting ratio, that can also be denoted as ⅓:⅓:⅓, corresponding to $α_{i,1}=α_{i,2}=α_{i,3}=⅓$, where i=1, 2, 3. Alternative embodiments of the invention may use couplers with other split ratios if desired.

Apart from the coupling coefficients $α_{i,j}$, a coupler is also characterized by phase shifts associated therewith, so that two optical waves entering the coupler through two different input ports will appear at the output ports with a phase that depends on the output port. This results in each output optical signal from the coupler having an interference component with its own phase that is generally different from the corresponding phase of the interference component of other optical output signals of the coupler, resulting in a phase shift $Δϕ_{j,j'}$ between interference components of optical signals output from different output ports j and j' of the coupler. In the case of a 2×2 coupler, this phase shift is known to be π and does not depend on the coupling coefficients $α_{i,j}$. However, for couplers with the number of output ports 3 and larger, the phase shift $Δϕ_{i,j}$ depends on the coupling coefficients $α_{i,j}$ and may generally differ from π. For example, if the 3×3 coupler has a splitting ratio of 33:33:33, meaning that the optical power input into one of the input ports 121, 122 is evenly distributed between the output ports 131-133, then the interference components at the coupler outputs will be out of phase by 2π/3, or 120 degrees.

In the shown embodiment, the M×N coupler 130 is by way of example a fiber-optic 3×3 coupler having 3 input ports and three output port, wherein one of the input ports is not used. Two output ports 131 and 133 of the 3×3 coupler 130 are each optically connected to an input port of two different differential detectors 150 and 155. Second input ports of the differential detectors 150 and 155 are coupled to the same remaining output port 132 of the 3×3 coupler 130 by means of a second beam splitter 135 embodied as a second 2×2 coupler, which has one of its two input ports unused. This novel output configuration of the Mach-Zehnder based interferometric system 101 of the present invention, wherein two differential detectors are each coupled to a different pair of output ports of an M×N coupler, is referred to herein as the dual-differential detection. Advantageously, it enables detection of both quadrature components of a complex sample-related interferometric signal, and simultaneous extraction of such optical characteristics of the sample as its absorption and refraction coefficients, as described herein below in further detail.

In operation, illumination light from a light source 105 is coupled into an input port of the beamsplitter 210, is then split in two light beams according to a pre-defined beam splitting ratio β of the beamsplitter 210, and the two light beams are directed along the reference and sample arms 115, 125, respectively, towards the 3×3 coupler 130, where light from the sample and reference arms is recombined, and the resulting light is evenly split between the three output ports 131-133 according to the ⅓:⅓:⅓ splitting ratio. In other embodiments, the coupler 130 can have a different splitting ratio. The light source 105 can be a broad-band light source, such a super-luminescent semiconductor diode, or a swept-wavelength source such as a continuously tunable laser.

Output optical power from each of the three output ports of the 3×3 coupler 130 has a component $S_i^{dc}$ which does not depend on the light wavelength or the time delay τ, which in this embodiment is the same for all three output signals from the coupler 130, i.e. $S_i^{dc}=S_{dc}$ for i=1,2,3 and will be hereinafter referred as the dc optical component, and an interferometric, or ac component $S_i$ which oscillates when either the light wavelength λ or the time delay τ is scanned; when light collected from the sample experienced a single reflection in the sample 140, the ac component $S_i$ can be approximately expressed as follows:

$$S_i=S_{ac}\cdot\cos(k\cdot\Delta x+\phi_j) \quad (2)$$

where j is an index indicating the output port of the coupler 130, i.e. j=1 corresponds to the output port 131, j=2 corresponds to the output port 132, and j=3 corresponds to the output port 133; k=2π/λ is the optical wavenumber, Δx=τc is the optical path length difference between the reference and sample arms, C(Δx) is the interferometric envelope accounting for the finite coherence length of the illumination light, and $\phi_j$ is the interferometric phase accounting for the optical phase shifts resulting from the light coupling within the coupler 130. Also, $$S_{ac}\approx\sigma\cdot S_0\cdot T_R\cdot T_S\cdot C(\Delta x) \quad (3)$$

is the magnitude of the interferometric component, which in this embodiment is the same for all three output signals from the coupler 130, $I_0$ is the optical power of the illumination light at the input port of the beamsplitter 210, $T_R$ and $T_S$ are amplitude transmission coefficients of the reference 115 and sample 125 arms, respectively, which accounts for optical losses in the arms, the sample reflectance and the splitting ratio of the input beamsplitter 210, σ ensures that the total power incident on the reference and sample arms is $I_0$, i.e. σ=⅓ for the exemplary case of a 3×3, 33:33:33 coupler that is considered herein.

The first differential detector 150 includes two constituent photo detectors 152 and 154 whose optical inputs serve as the two input ports of the differential detector 150, and a subtraction circuit 153 having an electrical output port 161; it receives and separately detects light from the first and second output ports 131, 132 of the coupler 130 using the two constituent photo detectors 152, 154. The electrical outputs of the photo detectors are passed to a subtraction circuit 155, which outputs, via the output port 161, a first output electrical signal $I_1$ that is equal to the amplified difference between the photocurrents produced by the two detectors 152, 154:

$$I_1=(g_1-0.5\cdot g_2)\cdot S_{dc}+S_{ac}[g_1\cdot\cos(k\cdot\Delta x+\phi_1)-0.5\cdot g_2\cdot\cos(k\cdot\Delta x+\phi_2)]\}, \quad (4)$$

where $g_1$ and $g_2$ are gain coefficients of the photo detectors 152 and 154, respectively, which account for their light-current conversion efficiency and any possible internal amplification.

Similarly, the second differential detector 155, which has the same internal structure as the first differential detector 150, receives and separately detects light from the third and second coupler outputs 131, 132, and produces, via an output port 162, a second output electrical signal $I_2$ which is equal to an amplified difference between photocurrents produced by two constituent photo detectors of the second differential detector 155:

$$I_2=(g_4-0.5\cdot g_3)\cdot S_{dc}+S_{ac}[g_4\cdot\cos(k\cdot\Delta x+\phi_3)-0.5\cdot g_3\cdot\cos(k\cdot\Delta x+\phi_2)]\}, \quad (5)$$

where $g_3$ and $g_4$ are gain coefficients of the photo detectors 157 and 158, respectively.

The output ports 161 and 162 of the differential detectors 150 and 155 are operatively coupled to a processor 190, wherein the first and second output electrical signals $I_1$ and $I_2$ are processed as described herein below.

Differential detection is known to provide improved signal to noise ratio (SNR) by canceling common mode noise, i.e. noise components that are common to signals received at each of the two input ports, when two optical signals with approximately equal dc power, but with ac components which are 180 degrees out of phase, are both present. The ac components of the optical signals $S_i$ provided by the output ports 131-133 of the coupler 130 have a phase shift there between that is not equal to π, and in particular may be equal to 2π/3 if the 3×3 coupler 130 has a 33:33:33 splitting ratio. Also, the dc components of the optical signals received in the input ports of the differential detectors 150 and 155, e.g. at the ports 148 and 149 of the differential detector 150, are not balanced since the output of the second port 132 of the coupler 130 is split in half between the two differential detectors 150 and 155 by the second beam splitter 135. As a result, each of the first and second output electrical signals $I_1$ and $I_2$ may have dc components $I_{1dc}=(g_1-0.5\cdot g_2)\cdot S_{dc}$ and $I_{2dc}=(g_4-0.5\cdot g_3)\cdot S_{dc}$ in addition to the desired ac, or interferometric components $I_{1ac}$ and $I_{2ac}$. In some embodiments, these dc components of the electrical signals output from the differential detectors 150 and 155 can be substantially eliminated by suitably adjusting the photo detector gain coefficients $g_i$, for example by selecting $g_1=0.5\cdot g_2$ and $g_4=0.5\cdot g_3$. However, we found that, even if all four photo detectors 152, 154, 157 and 158 have substantially equal gain, the differential detection realized in the shown in FIG. 3 scheme nevertheless provides a considerable SNR improvement compared to non-differential detection, despite the imbalance between the dc components of the input optical signal, and the phase difference between the ac components thereof which is not equal to 180 degrees, due to a suppression of the dc component relative to the ac component in the output electrical signals $I_1$ and $I_2$.

Figure 4:
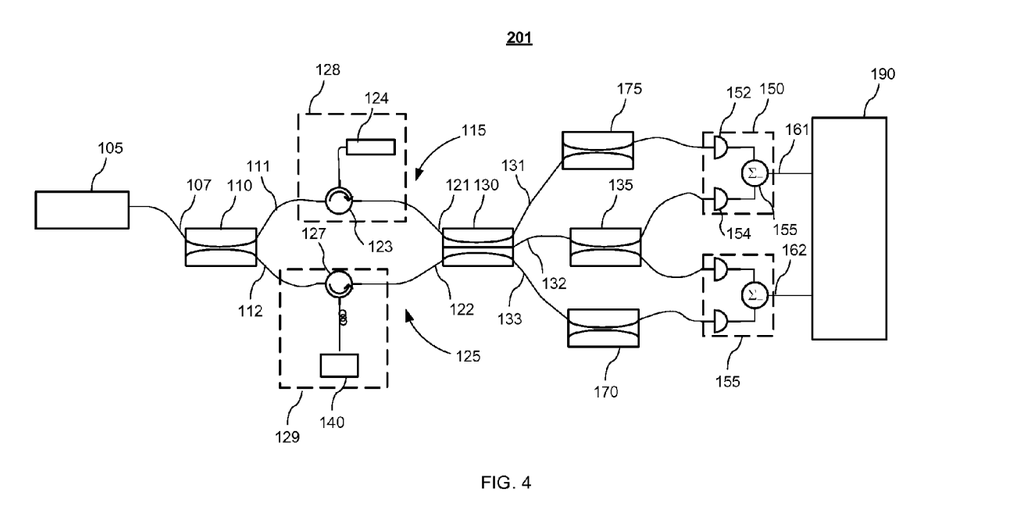
FIG. 4 is a diagram of a second embodiment of the interferometric system of the present invention utilizing a 3×3 coupler followed by three 2×2 couplers.

With reference to FIG. 4, an alternative second embodiment of the invention provides an interferometric system 201 which is similar to the interferometric system 101 shown in FIG. 3, but includes two additional optical attenuators 170 and 175, in the shown configuration embodied as 2×2 couplers, that are coupled between the first 131 and third 133 ports of the 3×3 coupler 130 and respective optical input ports of the differential detectors 155 and 150, so as to equalize dc components of the optical signal at both ports of each of the differential detectors 150 and 155. In this embodiment, the differential detectors 150 and 155 are balanced so as to provide electrical output signals wherein the dc components are substantially canceled, thereby providing optimal cancellation of common mode noise.

In both embodiments, the ac, or interferometric components $I_{1ac}$, $I_{2ac}$ of the first and second electrical signals that are output through the ports 161 and 162 have a phase shift Δφ that is not equal to π or any integer multiple thereof, and may for example be equal to π/3 if the 3×3 coupler 130 has the splitting ratio 33:33:33. Advantageously, this enables one to simultaneously obtain two quadrature components of a complex interferometric signal, and thus provide more information about the sample 140 under investigation by performing suitable data processing. For this purpose, the first and second electric signals $I_{1,2}$ are first digitized using analog-to-digital converts (not shown), and then passed to the processor 190, which is programmed to subtract their dc components if present, which can be done, for example, by first collecting and storing required calibration data. The remaining digitized ac components $I_{1ac}$, $I_{2ac}$ are further processed to obtain two quadrature interferometric signal components, and to extract information related to the sample 140. This can be done, for example, as follows.

Assuming that the differential detectors 150 and 155 are substantially identical, the ac components of the first and second electrical signals can be expressed as $$I_{1ac} = \kappa \cdot S_{AC} \cdot \cos(k\Delta x + \phi_0), \quad (6)$$

and $$I_{2ac} = c \cdot S_{AC} \cdot \cos(k\Delta x + \phi_0 + \Delta\phi), \quad (7)$$

where c is a proportionality coefficient dependent on the photo detectors internal gain and conversion coefficients, and $\phi_0$ is a potion of the phase shift which is common to both detection channels. Using these signals, real $I_{RE}$ and imaginary $I_{IM}$ components of a complex interferometric signal $I = c \cdot S_{AC} \cdot \exp(i \cdot k \cdot \Delta x + \phi_0)$, which are also referred to as the quadrature components, are then computed using the following trigonometric equations:

$$I_{RE} = I_{1ac}, \quad (8)$$

$$I_{IM} = \frac{I_{1ac}\cos(\Delta\phi) - I_{2ac}}{\sin(\Delta\phi)}, \quad (9)$$

where in (9) $\Delta\phi \neq 0$. The quadrature signals $I_{RE}$ and $I_{IM}$ can be used to provide spatially resolved information about the sample 140. For this purpose, the interferometric system 101 includes means to change relative position of the sample 140 and the fiber end 141 in response to a control signal from the processor 190, for example as shown in FIG. 3. This may include a movable sample holder 143 to which the sample 130 is mounted, and which can be moved in x, y and z directions relative to the stationary fiber end 141 in response to a signal from a driver 165 controlled by the processor 190. Alternatively, a spatial position of the fiber end 141 can be controlled, and the sample 140 can be stationary, or a scanning optics can be used between the sample 140 and the fiber end 141. An A-scan is obtained by varying the time delay provided by the variable optical delay line 124 in response to a control signal from the processor 190, or optionally by moving the sample in the z direction so as to change the distance between the sample and the fiber end 141 and thus the optical path difference Δx, so as to provide depth-resolved measurements. A B-scan is obtained by moving the sample in the x or y directions. The processor 190 includes memory for storing the imaginary and real parts of the complex interferometric signal for a plurality of optical time delay values, and for storing a coherence function of the light source for the plurality of optical time delay values. In operation, the processor 190 computes the quadrature interferometric signals $I_{RE}$ and $I_{IM}$ from the received first and second electrical signals at a set time interval while varying the time delay provided by the delay line 124 for each position of the sample 140 relative to the fiber end 141, and stores the computed values in relation to the time delay values for each sample position.

The embodiment of FIG. 3 has been tested using a broadband Super Luminiscent Diode available from COVEGA, with an output power of 10 mW, $\lambda_0=1310$ nm, $\Delta\lambda=70$ nm and a 3×3 fiber coupler for operating wavelength range 1250-1380 nm available from OPLINK Communications.

Figure 5:
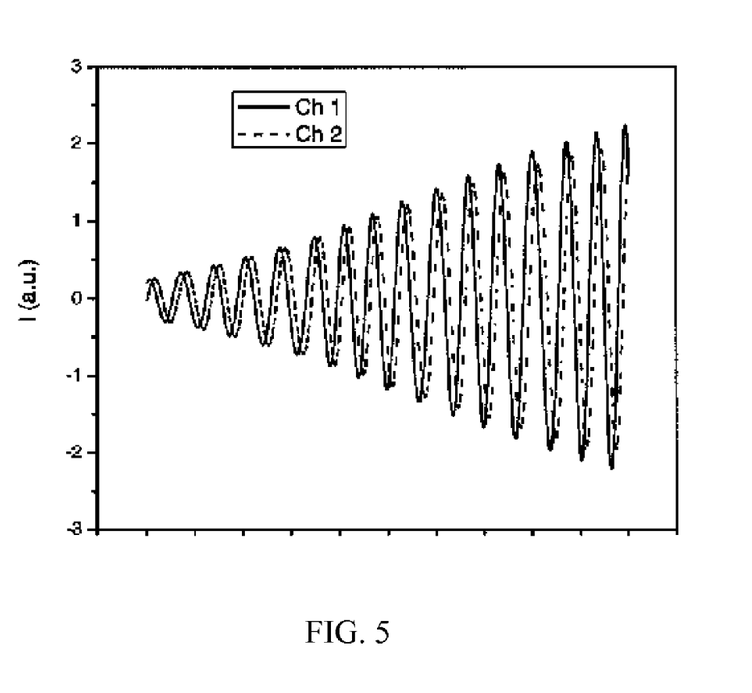
FIG. 5 is a plot of electrical signals detected by the first and second differential detectors of the interferometric system shown in FIG. 3.

FIG. 5 shows a portion of a dual-channel A-scan interferogram obtain by the interferometric system 101 using a glass plate in place of the sample 140; the interferogram corresponds to a sharp change of the refractive index at the air-glass interface. The dashed and solid curves represent the dependence of the ac components of the first and second electrical signals as measured by the differential detectors 150 and 155, respectively, upon the optical path difference Δx in the sample and reference arms; the measured ac signal components have a relative phase shift of approximately 60 degrees, or π/3.

Figure 6:
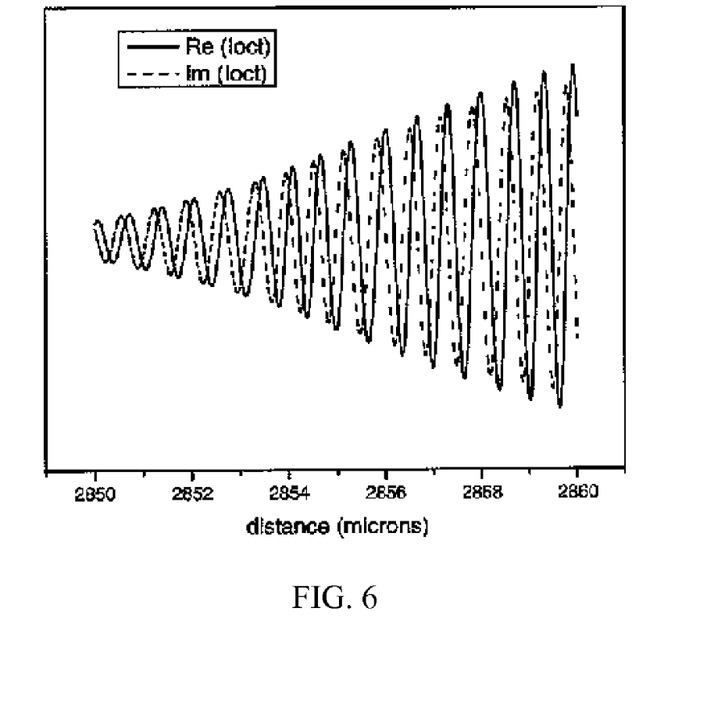
FIG. 6 is a plot of the real and imaginary parts of a complex interferometric signal computed using the detected electrical signals shown in FIG. 5.

FIG. 6 shows the real and imaginary components $I_{RE}$ and $I_{IM}$ of the complex interferometric signal I computed from the measured ac signals shown in FIG. 5; they have a phase shift of π/2.

Figure 7:
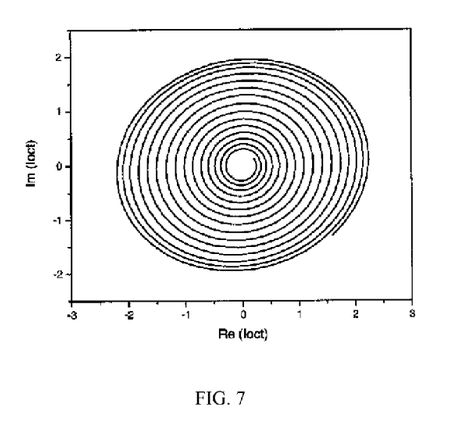
FIG. 7 is a Lissajous plot showing the imaginary part of the complex interferometric signal shown in FIG. 6 as a function of its imaginary part.

Signals $I_{RE}$ and $I_{IM}$ FIG. 7 shows a Lissajous plot of the interferometric signal shown in FIG. 6, obtained by parametrically plotting the real and imaginary components $I_{RE}$ and $I_{IM}$ against each other; the characteristic shape of the curve confirms that the signals $I_{RE}$ and $I_{IM}$ indeed constitute a quadrature pair.

Advantageously, we found that the interferometric system 101 shown in FIG. 3 is characterized by an SNR which is 10-20 dB higher than the SNR of the prior art Michelson-based interferometric system, such as the system similar to that shown in FIG. 2, due to the use of differential detection and better optical power management provided by the Mach-Zehnder based system of the present invention. We also found that the SNR of the interferometric system 101 is about 3 dB higher than the SNR of a Michelson-based interferometric system that uses differential detection. However, the differential detection suppresses only the common mode noise, and can be sensitive to environmental changes that affect the sample and reference arms 125, 115 differently. Differential phase changes in both arms could be produced by changes in the ambient temperature, by movement of optical fibers connecting different elements within the sample and reference arms 115 and 125, and by polarization changes within the optical fiber. Under laboratory conditions and clinical environment, these perturbations can be reduced but at a priced by an increased complexity of the setup.

Figure 8:
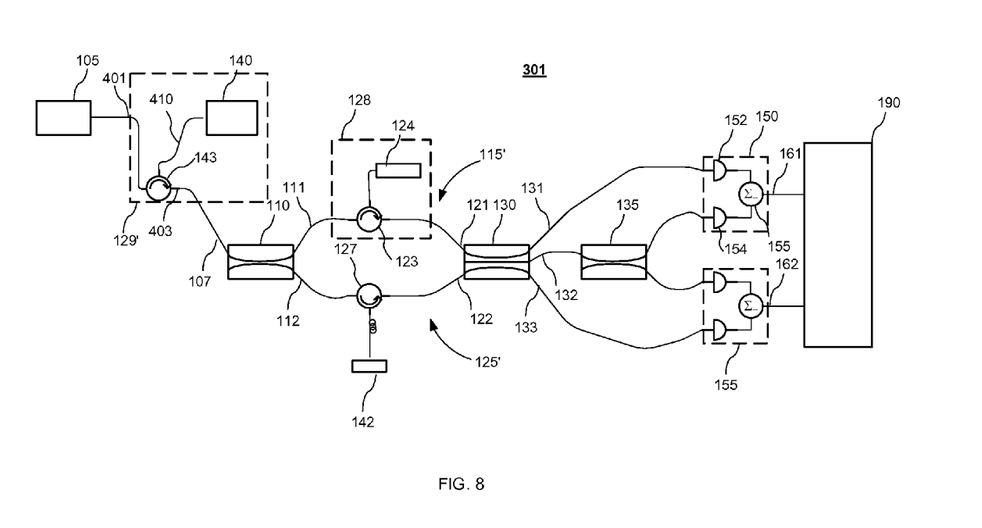
FIG. 8 is a diagram of a third embodiment of the interferometric system of the present invention utilizing a Fizeau interferometer to collect light from the sample.

An embodiment of the present invention which is more robust to environmentally-induced differential changes in the system is shown in FIG. 8. As before, like elements in FIGS. 3 and 8 are represented by like reference numerals. An interferometric system 301 illustrated in FIG. 8 has many of the same elements as the interferometric system 101 of FIG. 3. A main difference between these two systems is that the sample illuminating means, which is shown in FIG. 8 at 129', is now includes a Fizeau-type fiber-sample interferometric arrangement, which is located at the input end of the system between the light source 105 and the first beamsplitter 210, and prior to the Mach-Zehnder interferometer formed by two connecting arms 115' and 125'. The interferometric system 301 is thus based on a dual Fizeau-Mach-Zehnder interferometry and utilizes the advantages of both these interferometric topologies.

Similar to the sample illuminating means 129 of the interferometric system 101, the sample illuminating means 129' includes the optical circulator 143 having three fiber-optic ports, with a middle port connected to a first end of an optical fiber 410 for illuminating the sample 140 and for collecting light reflected there from. The circulator 143 also has a first, or input port 401 coupled for receiving illumination light from the light source 105, and a third, or output port 403 coupled to the input port 107 of the first beamsplitter 210.

Figure 9:
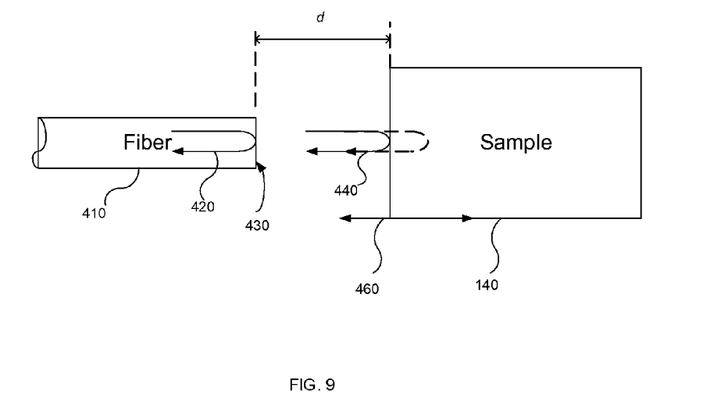
FIG. 9 is a diagram of the light collecting portion of the interferometric system shown in FIG. 8.

The interferometric arrangement used in the sample illuminating means 129' of the interferometric system 301 is schematically illustrated in FIG. 9, which shows an end portion of the optical fiber 410 positioned close to the sample 140 with a small gap d there between, which can be between a few microns and a few centimeters and can optionally include a focusing or collimating optics. The optical fiber 410 has a partially reflecting second end 430 which faces the sample 140, so that light propagating in the fiber 410 from the circulator 143 is split at the fiber end 430 into two portions. A first portion 420 is immediately reflected back into the fiber 410 without leaving the fiber and forms reference light, so that the partially reflecting fiber end 430 serves as a reference reflector for providing reference light to the input port 107 of the first beamsplitter 210. A second portion 440 is transmitted towards the sample 140, wherefrom it is partially reflected or scattered back towards the fiber end 430, is collected by the fiber and is guided back towards the circulator 143 together with the light potion 420 reflected from fiber end 430.

The partially reflecting fiber end 430 is cleaved and/or polished to provide approximately 4% reflectance; optionally a partially reflecting coating can be utilized to increase the fiber end reflectivity if desired.

The circulator 143 couples combined light consisting of the reference light 420 and the light 440 collected from the sample into the input port 107 of the first beamsplitter 210, which splits the combined light in two portions, each including light reflected from the sample and reference light, and directs these two portions along the two connecting arms 115' and 125' of the Mach-Zehnder interferometer towards the 3×3 coupler 130. The first connecting arm 115' includes the time delay means 128 including the variable optical delay line 124 as described hereinabove with reference to the first embodiment shown in FIG. 3. In operation, the variable delay line 124 is tuned so that the optical path length difference $\Delta x$ between the first and second connecting arms 115' and 125' is approximately equal to or greater than the sample-fiber distance d, with the length difference ($\Delta x - d$) determining the depth within the sample wherefrom the measurements are taken. The second arm 125' includes an optional delay line for roughly equalizing the optical path lengths of the first and second arms 115', 125', formed by the circulator 127 and a mirror 142, so that to lessen requirements on the dynamic range of the variable delay line 124.

As shown in FIG. 8, the output light detection arrangement of the interferometric system 301 includes the second beam splitter 135 and two differential detectors 150, 155, and is substantially identical to that of the FIG. 3 system, and provides dual-channel differential detection for obtaining the quadrature interferometric signals $I_{RE}$ and $I_{IM}$ using the processor 190, which can be embodied for example as a general purpose computer including data acquisition card or cards, or using a microprocessor, a DSP, an FPGA, or a combination thereof.

Advantageously, the reference light and light collected from the sample in the interferometric system 301 propagate along substantially the same optical paths, through the same optical fibers and the same optical elements, and therefore are subject to identical environmentally-induced fluctuations, which can therefore be automatically canceled by the differential detection. As a further advantage, in this configuration most of the illumination light, for example about 80% for a typical circulator loss about 1 dB, can be used for sample illumination. This is an important advantage for biological samples, from which only a very small fraction of light, often in the order of $10^{-5}$ or less, can be collected back into the system.

The interferometric system of the present invention has been described hereinabove with reference to exemplary embodiments thereof such as those illustrated in FIGS. 3, 4 and 8. These embodiments use a 3×3 coupler 130 at the output element of the constituent Mach-Zehnder interferometer to provide optical signals having an interferometric phase shift that differs from $\pi$, so that both quadrature components can be simultaneously extracted. Alternatively, other M×N couplers with N>2 can be also used in place of the coupler 130 according to the present invention.

Figure 10:
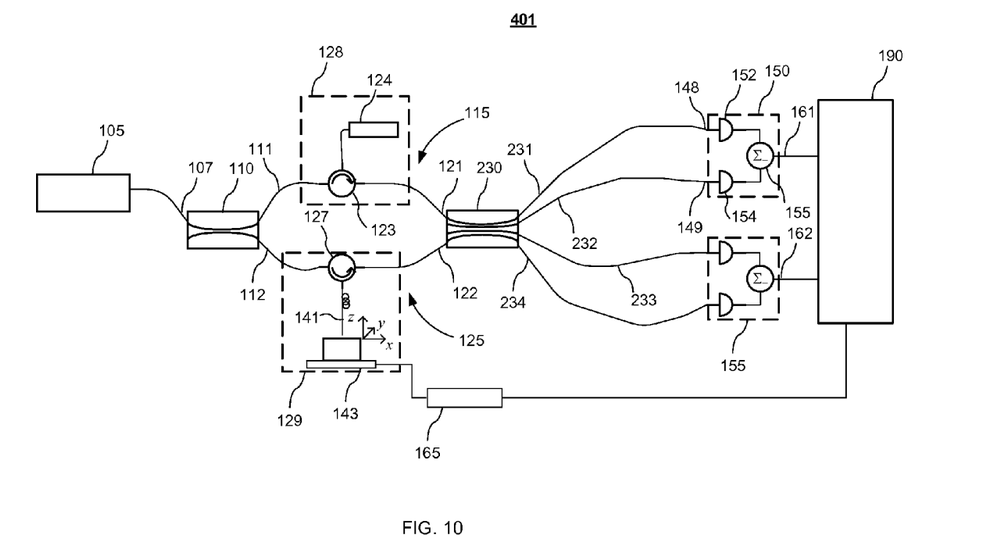
FIG. 10 is a diagram of a fourth embodiment of the interferometric system of the present invention utilizing a 4×4 coupler.

Such an embodiment is illustrated in FIG. 10 showing an interferometric system 401, which utilizes a 4×4 coupler 230 in place of the 3×3 coupler 130. Preferably, the 4×4 coupler 230 has a splitting ratio 25:25:25:25, meaning the light coupled to any of the input ports of the coupler is output from its four output ports 231-234 in equal portions. Advantageously, interferometric components at the output ports of such a coupler are characterized by phase shifts $\phi_n$ which differ from one port to another by $\pi/2$. By way of example, an interferometric component of light output from port 231 has a phase $\phi_1=0$, an interferometric component of light output from port 233 has a phase $\phi_1=\pi/2$, an interferometric component of light output from port 232 has a phase $\phi_1=\pi$, and an interferometric component of light output from port 234 has a phase $\phi_1=3\pi/2$. Accordingly, the output ports of the coupler 230 can be pair-wise directly connected to input ports of the differential detectors 150 and 155 as shown in FIG. 10, which in this case provide balanced differential detection so that the dc components of the received optical signals are substantially canceled. Furthermore, in this embodiment the first and second output electrical signals generated by the differential detectors 150 and 155 are two quadrature interferometric signals, and can be directly utilized as the real and imaginary parts $I_{RE}$ and $I_{IM}$ of the complex interferometric signal by the processor 190.

The aforedescribed interferometric system of the present invention realizes dual differential detection to simultaneously generate two quadrature interferometric signals, which represent real and imaginary parts of the complex interferometric signal. The system of the present invention can be used in both homodyne and heterodyne OCT systems; the heterodyne approach can be realized, for example, by adding an optical modulator to one of the connecting arms 115, 125 of the Mach-Zehnder interferometer. The light source 105 can be a broad-band light source, in which case the aforedescribed interferometric systems can be used for low-coherence time-domain OCT (TD-OCT), when the axial, i.e. depth, ranging is provided by linearly scanning in time the optical path length difference between the interferometer sample and reference arms.

Other embodiments can use a narrowband wavelength-swept laser as the light source 105, in which case a Fourier-based swept-source OCT (SS-OCT) technique can be employed using the interferometric system of the present invention. In SS-OCT, the location of scatter centers within the sample, for example a tissue, is derived by the Fourier transformation of an interferogram, which is obtained by recording the interferometric signal while the light wavelength is swept. If only the real components of the interferometric signal is used, the Fourier transform of the interferogram, which is Hermitian symmetric, introduces a complex conjugate artifact in which positive and negative distances are not resolved, thus only a half of the total imaging depth can be utilized. The interferometric system of the present invention enables to obviate the problem of the complex conjugate artifact, which is also referred to as the depth-degeneracy, by providing simultaneously both the real and imaginary parts of the interferogram, thereby enabling to increase imaging depth in SS-OCT applications. Experimental results related to SS-OCT imaging using the system of the present invention are described in an article entitled "Sensitivity Investigation of Instantaneous Complex Conjugate Resolved Swept-Source OCT Using a Mach-Zehnder Interferometer with a 3×3 Fiber Coupler" by Youxin Mao, Costel Flueraru, Sherif, Shoude Chang, and E. Murdock, SPIE Proceeding of Photonics North 2007 (in press), which is incorporated herein by reference for all purposes.

Another aspect of the present invention provides a method for simultaneously obtaining refractive and absorptive properties of a sample, which can be realized using the interferometric system of the instant invention, for example any of the embodiments described hereinabove with reference to FIGS. 3, 4, 8 and 10. This method can be advantageously used for complex image extraction and restoration in OCT and OLCR, to provide depth-resolve imaging of the sample wherein images of the sample refraction and absorption coefficients are simultaneously obtained.

The method is based on the following considerations.

An optical image of a sample may represent a spatial distribution of its refractive index, n(r), where r=(x, y, z) is the location vector within the sample. Since most samples absorb part of the illumination light used to image them, the refractive index n(r) can be considered as a complex valued function, $n(r)=n_{real}(r)+j\cdot n_{imag}(r)$, where $n_{real}(r)$ and $n_{imag}(r)$ represent, respectively, the refraction and absorption properties of the sample. In the following, we will be referring to the complex-valued function n(r) as the complex refractive index, and the real-valued function $n_{real}(r)$ as the refraction coefficient. The imaginary part $n_{imag}$ of the complex refraction function n(r) relates to an absorption coefficient $\alpha_a$ as follows:

$$\alpha_a = 4\pi n_{imag}/\lambda \quad (10)$$

where $\lambda$ is the light wavelength.

The magnitude of the interferometric component $S_{ac}$ of light, which carries the sample information, is a function of the optical time delay $\tau$ between the sample and reference light, $S_{ac}=S(\tau)$, and is proportional to a convolution of the so-called scattering potential of the sample $F(\tau)$ with the coherence function of the light source $\gamma(\tau)$:

$$S(\tau) \propto F(\tau) \otimes \gamma(\tau), \quad (11)$$

where $\otimes$ is the convolution operator.

For a weakly scattering object the time delay $\tau$ is linearly proportional to the depth position, z, such that both variables are interchangeable, and we can write $n(r)=n(\tau)$, where for now the dependence of the refractive index on the x and y coordinates in plane of the sample's surface is omitted.

The scattering potential within the sample satisfies the following proportionality relationship:

$$F(\tau) \propto (n^2(\tau)-1) = [n_{real}^2(\tau) - n_{imag}^2(\tau) - 1 + 2jn_{real}(\tau)n_{imag}(\tau)]. \quad (12)$$

In a conventional OCT system, the detected signal is proportional to the real part of this interferometric signal $S(\tau)$:

$$I(\tau) \propto Re\{F(\tau) \otimes \gamma(\tau)\}, \quad (13)$$

A drawback of this approach is that certain information about the sample which is is contained in the imaginary part of the interferometric signal is lost; another drawback is that in the detected signal the absorption and refraction effects are mixed together, which makes it very difficult, if at all possible, to reliably separate them and to obtain the refraction and absorption characteristics of the sample individually.

Advantageously, the interferometric system of the present invention obtains both the real and imaginary parts of the complex interferometric signal simultaneously, and therefore it becomes possible to separately extract the absorption and refraction properties of the sample from the measured interferometric data. This can be done by relating the obtained complex interferometric signal $I=I(\tau)$ to the complex convolution of the scatter potential $F(\tau)$ and the known complex coherence function of the illumination light $$\gamma(\tau) = \frac{\langle U^*(t) \cdot U(t+\tau) \rangle}{\langle U^*(t) \cdot U(t) \rangle},$$

where U is the complex electric field of the illumination light, and a superscript "*" denotes complex conjugate and $\langle \rangle$ represent the average over time:

$$I(\tau) = aF(\tau) \otimes \gamma(\tau), \quad (14)$$

where a is a proportionality constant that can be determined by calibration, for example using a sample with known optical properties. By performing a complex deconvolution of the obtained complex interferometric signal $$I(\tau) = I_{RE}(\tau) + j \cdot I_{IM}(\tau), \quad (15)$$

with the complex coherence function $\gamma(\tau)$, and equating the result with the scatter potential $F(\tau)=(n^2(\tau)-1)$, the depth-resolved refraction and extinction coefficients at a particular sample location from which the light was collected can be obtained using the following equations:

$$n_{real}(\tau) = Re\{\sqrt{F(\tau)+1}\}, \quad (16)$$

$$\kappa(\tau) = -Im\{\sqrt{F(\tau)+1}\} \quad (17)$$

where Re {} and Im {} denote real and imaginary parts of {}.

Figure 11:
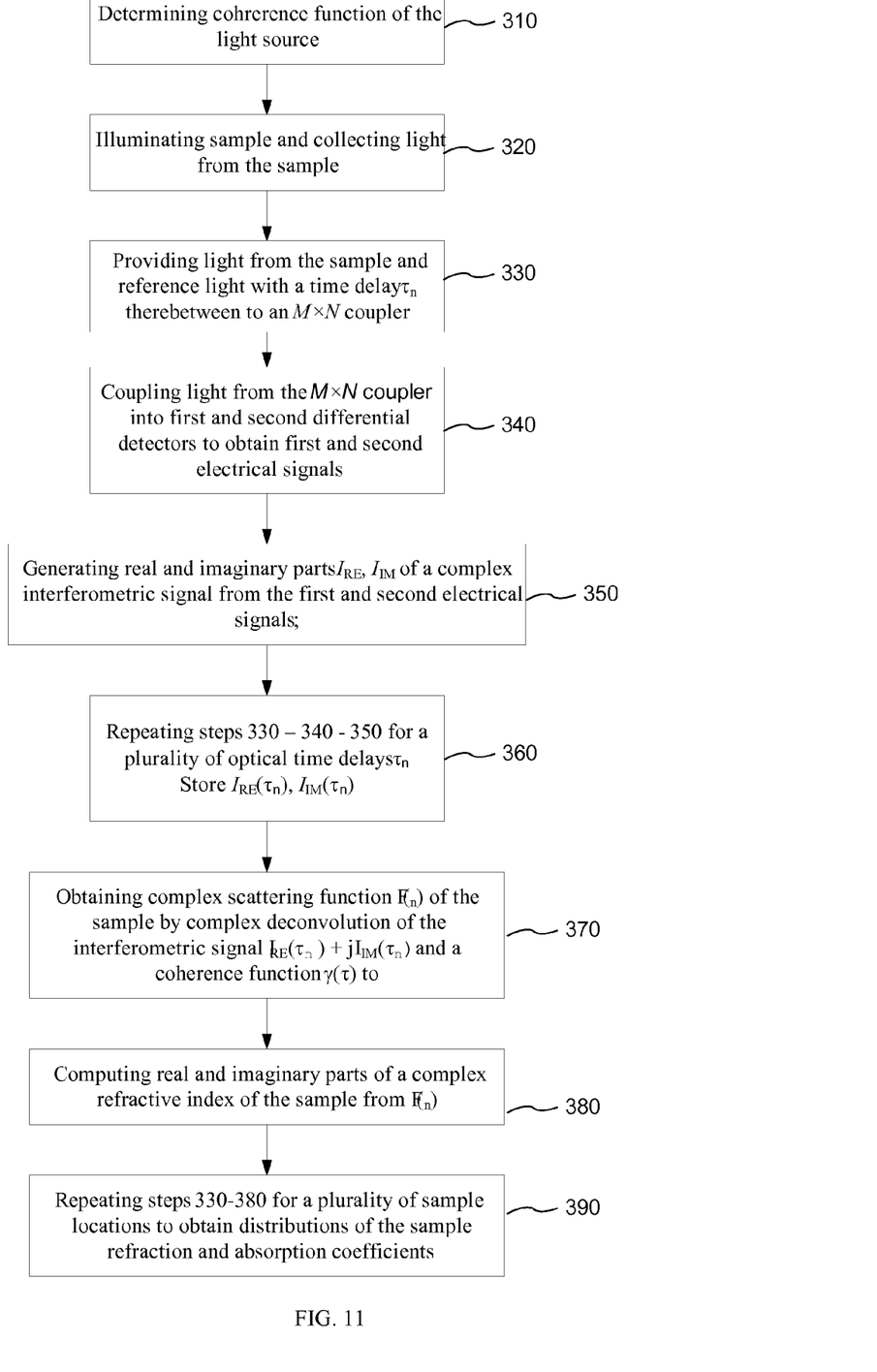
FIG. 11 is a flowchart showing main steps of the method of the present invention for imaging absorption and refraction coefficients of the sample.

An exemplary embodiment of the method of the present invention for simultaneously determining refractive and absorptive properties of a sample is illustrated in FIG. 11 and will now be described with reference to an embodiment of the interferometric system of the present invention, such as that shown in FIGS. 3, 4, 8 and 10, wherein the light source 105 emits broadband light.

With reference to FIG. 11, the method includes the following steps 310-390.

Step 310: determining the coherence function $\gamma(\tau)$ of the broadband light source for a plurality of time delays $\tau$ is determined, and saving it, e.g. in memory 195 of the processor 190. This can be done, for example, using a suitable reference mirror in place of the sample 140, recording signals from the differential detectors 150 and 155 while scanning the variable delay line 124 to vary the time delay $\tau$ in a desired range, and computing the real and imaginary parts of the interferometric signal using for example equations (8) and (9) to obtain envelope functions thereof.

Step 320: illuminating a selected location in the sample under investigation with a portion of the broadband light, and collecting light reflected or scattered from the sample;

Step 330: providing light collected from the sample to an input port of an M×N optical coupler having M≧2 input ports and N≧3 output ports, while simultaneously providing a reference portion of the broad band light into another input port of the M×N optical coupler. The M×N coupler can be a 3×3 coupler 130 shown in FIGS. 3, 8, and 10, or any other multiport coupler having at least 2 input ports and 3 or more output ports, such as the 4×4 coupler shown in FIG. 8.

Step 340: coupling light from a first two of the N output ports of the M×N coupler into a first differential detector to obtain a first electrical signal, and coupling light from a second two of the N output ports of the M×N coupler into a second differential detector to obtain a second electrical signal. This is illustrated for example in FIG. 3, where light from the first two output ports of the coupler 130, i.e. the ports 131 and 132, is coupled into the first differential detector 150, while light from the second two output ports of the coupler 130, i.e. the ports 132 and 133, is coupled into the first differential detector 155; note that in the context of this specification two pairs of ports are considered to be different if they differ by at least one port.

Step 350: generating real and imaginary parts $I_{RE}$, $I_{IM}$ of a complex interferometric signal I from the first and second differential signals; in the embodiments shown in FIGS. 3, 4 and 10 which utilize the 3×3 coupler 130, this can be done using equations (8) and (9), i.e. by designating one of the first and second electrical signals obtained from the differential detectors 150, 155 to represent the real part $I_{RE}$ of the complex interferometric signal I, and using a simple trigonometric transformation to compute the imaginary part $I_{IM}$ thereof on the basis of both the first and second electrical signals;

Step 360: repeating steps 330-340-350 for a plurality of optical time delays $\tau_n$ between the reference light and light collected from the sample, and store in memory (195) the generated values $I_{RE}(\tau_n)$ and $I_{IM}(\tau_n)$ as functions of the optical time delay $\tau_n$;

Step 370: performing complex deconvolution of the complex interferometric signal $I(\tau_n)=I_{RE}(\tau_n)+j \cdot I_{IM}(\tau_n)$ and the stored coherence function $\gamma(\tau)$ of the broadband light to obtain the depth-resolved complex scattering function of the sample $F(\tau_n)$; various methods of complex deconvolution, and computer algorithms implementing these methods, are known in the art and can be used in the method of the present invention, for example by suitably programming the processor 190 to perform a selected deconvolution algorithm;

Step 380: computing real and imaginary parts of a complex refractive index of the sample from the real and imaginary parts of the depth-resolved complex scattering function of the sample, for example using equations (16) and (17); and, Step 390: repeating steps 330-380 for a plurality of sample locations to image the distribution of the refraction and absorption coefficients across the sample.

In another embodiment, instead of combining the generated real and imaginary signals $I_{RE}$ and $I_{IM}$ and performing the complex deconvolution thereof with the saved complex coherence function, two real-valued deconvolutions can be performed in step (h) to obtain the refraction and absorption coefficients Advantageously, the method of the present invention, which utilizes the dual differential detection provided by the novel interferometric systems described hereinabove, provides instantaneous complex deconvolution of OCT images, and yields simultaneously and separately both the optical propagation and loss properties of an object.

Although the invention has been described hereinabove with reference to particular embodiments thereof, it should be understood that theses embodiments are examples only and should not be construed as limiting the invention. It should also be understood that each of the preceding embodiments of the present invention may utilize a portion of another embodiment.

Of course numerous other embodiments of the method of system of the present invention may be envisioned without departing from the spirit and scope of the invention.

We claim:

1. A system for detecting optical characteristics of a sample, comprising:

an interferometer for mixing light collected from the sample with reference light for interfering therewith, the interferometer comprising:

a first optical coupler having two input ports connected for receiving reference light and light collected from the sample, and at least three output ports;

a first differential detector having two input optical ports coupled to a first two of the at least three output ports of the optical coupler for providing a first electrical signal having a first interferometric component; and, a second differential detector having two input optical ports coupled to a second two of the at least three output ports of the optical coupler for providing a second electrical signal having a second interferometric component;

wherein the first optical coupler is such that the first and second interferometric components have a relative phase shift therebetween that is not an integer multiple of π, so as to provide information separately characterizing real and imaginary components of a complex interferometric signal related to the sample.

2. A system according to claim 1, wherein the interferometer further comprises a first beam splitter having two output ports coupled to the two input ports of the first optical coupler using two connecting arms, and an input port.

3. A system according to claim 2, wherein one of the two connecting arms includes a time delay means for providing a variable optical time delay to light propagating in said connecting arm.

4. A system according to claim 2, wherein the first optical coupler comprises an N×N fiber-optic coupler having N input ports and N output ports.

5. A system according to claim 4, wherein N=3.

6. A system according to claim 5 further comprising a second beamsplitter connected to one of the output ports of the first optical coupler for coupling light therefrom into each of the two differential detectors.

7. A system according to claim 3, wherein one of the two connecting arms comprises a sample illuminating means for illuminating the sample and for directing the light collected from the sample to one of the input ports of the first optical coupler.

8. A system according to claim 3, further comprising;

a sample illuminating means for illuminating the sample and for directing light reflected from the sample to the input port of the first beam splitter, the sample illuminating means including a reference reflector for providing the reference light to the input port of the first beamsplitter.

9. A system according to claim 8, wherein the sample illuminating means includes an optical circulator having an input port for coupling to a light source, an output port coupled to the input port of the first beam splitter, and a middle port for providing light for illuminating the sample, and for receiving light collected from the sample and the reference light, and for directing received light to the output port.

10. A system according to claim 9, wherein the sample illuminating means further includes an optical waveguide having a first end coupled to the middle port of the optical circulator for receiving the illumination light, and a partially reflecting second end as the reference reflector for reflecting back into the optical fiber a first portion of the illumination light incident thereon for forming the reference light, wherein said second end is arranged for illuminating the sample therethrough and for collecting a second portion of the illumination light that is reflected from the sample back into the optical fiber for coupling into the input port of the first beamsplitter together with the first portion.

11. A system according to claim 1, further comprising a light source for illuminating the sample.

12. A system according to claim 1, further comprising a processor operatively coupled to the first and second balanced detectors for generating real and imaginary parts of the complex interferometric signal from the first and second differential electrical signals.

13. A system according to claim 12, wherein the processor includes memory for storing the imaginary and real parts of the complex interferometric signal for a plurality of optical time delay values, and for storing a coherence function of the light source for the plurality of optical time delay values.

14. A system according to claim 13, wherein the processor is programmed to compute a refractive index parameter and an absorption parameter for the sample by
   a) combining the real and imaginary parts of the interferometric signal to form the complex interferometric signal for the plurality of optical delay values;
   b) using a deconvolution algorithm, performing a complex deconvolution of the complex interferometric signal and the coherence function to obtain a complex scattering function; and,
   c) computing real and imaginary parts of a complex refractive index parameter from real and imaginary parts of the complex scattering function.

15. A method for simultaneously obtaining refractive and absorptive properties of a sample, the method comprising the steps of:
   illuminating the sample with a portion of broadband light and collecting light from the sample;
   providing light collected from the sample to an input port of an M×N optical coupler having M input ports and N output ports, while simultaneously providing a reference portion of the broad band light into another input port of the M×N optical coupler, wherein N≧3 and M≧2;
   coupling light from a first two of the N output ports of the M×N coupler into a first differential detector to obtain a first electrical signal;
   coupling light from a second two of the N output ports of the M×N coupler into a second differential detector to obtain a second electrical signal;
   generating real and imaginary parts of a complex interferometric signal from the first and second differential signals;
   performing complex deconvolution of the complex interferometric signal and a coherence function of the broadband light to obtain depth-resolved complex scattering function of the sample; and,
   computing real and imaginary parts of a complex refractive index of the sample from the real and imaginary parts of the depth-resolved complex scattering function of the sample.

16. An interferometric system for detecting optical characteristics of a sample, comprising:
   a Mach-Zehnder interferometer for providing a variable optical delay between light collected from the sample and reference light, the Mach-Zehnder interferometer comprising an output M×N coupler for mixing the light collected from the sample with the reference light for interfering therewith, the M×N coupler having N≧3 output ports; and,
   first and second differential detectors, each having two input ports coupled to a different two of the N output ports of the M×N coupler, for producing first and second electrical signals having an interferometric phase shift therebetween, wherein said interferometric phase shift is not equal to an integer multiple of π radians.

17. An interferometric system according to claim 16, further comprising a beam splitter optically coupled between the M×N coupler and the first and second differential detectors to couple light from one of the output ports of the M×N coupler into each of the differential detectors.

18. An interferometric system according to claim 16, further comprising a processor coupled to receive the first and second electrical signals and programmed to compute refraction and absorption coefficients therefrom using a stored coherence function and a deconvolution algorithm.

* * * * *